(12) United States Patent
Keller et al.

(10) Patent No.: US 6,753,459 B2
(45) Date of Patent: Jun. 22, 2004

(54) TRANSGENIC PLANTS AND METHODS FOR PRODUCTION THEREOF

(75) Inventors: Wilfred A. Keller, Saskatoon (CA); Steven F. Fabijanski, Orleans (CA); Paul G. Arnison, Orleans (CA); Joseph K. Hammerlindl, Saskatoon (CA); Steven R. Webb, Saskatoon (CA)

(73) Assignees: National Research Council of Canada (CA); Dow Agrosciences LLC

( * ) Notice: Subject to any disclaimer, the term of this patent is extended or adjusted under 35 U.S.C. 154(b) by 8 days.

(21) Appl. No.: 09/886,207

(22) Filed: Jun. 22, 2001

(65) Prior Publication Data

US 2003/0188329 A1 Oct. 2, 2003

Related U.S. Application Data

(63) Continuation of application No. PCT/CA99/01223, filed on Dec. 22, 1999.
(60) Provisional application No. 60/113,546, filed on Dec. 22, 1998.

(51) Int. Cl.$^7$ .................. C12N 15/82; C12N 15/31; C12N 15/12; A01H 5/00
(52) U.S. Cl. .................. 800/278; 800/281; 800/284; 800/286; 800/288; 800/289; 800/294; 800/300; 435/69.1; 435/252.2; 435/320.1; 435/430.1; 435/431
(58) Field of Search ................ 800/278, 281, 800/284, 286, 288, 289, 294, 300; 435/69.1, 431, 252.2, 320.1, 430.1

(56) References Cited

U.S. PATENT DOCUMENTS 5,254,801 A  10/1993  Dotson et al. ............. 800/205
5,278,057 A  1/1994  Jorgensen ................. 435/172.3
5,426,041 A  6/1995  Fabijanski et al. ........ 435/172.3
5,550,038 A * 8/1996  Goodman et al. ......... 435/70.1
5,777,201 A  7/1998  Poutre et al. ............... 800/250

FOREIGN PATENT DOCUMENTS

EP  0198288  10/1985
EP  0636310  2/1995
WO  9740179  10/1997

OTHER PUBLICATIONS

Kriete et al. The Plant Journal 9(6): 809–819 1996.*
Medford et al. The Plant Cell 1: 403–413, Apr. 1989.*
Smigocki et al. Proc. Natl. Acad. Sci. USA 85: 5131–5135, Jul. 1988.*
Derwent World Patent Index, Abstract No. 1986–157860, (May 7, 1986).
Derwent World Patent Index, Abstract No. 1988–333483, (Oct. 12, 1988).
Zou J. et al. 1997. Modification of Seed Oil Content and Acyl Composition in the Brassicaceae by Expression of a Yeast sn–2 Acyltransferase Gene. The Plant Cell. 9:909–923.

* cited by examiner

Primary Examiner—David T. Fox
(74) Attorney, Agent, or Firm—Lorusso, Loud & Kelly

(57) ABSTRACT

Genetic constructs, transformation vectors and methods are taught for production of transgenic plants which can be selectively removed from a growing site by application of a chemical agent or physiological stress. The invention links a target gene for the trait of commercial interest to a conditionally lethal gene, which can be selectively expressed to cause plant death. By use of the genetic constructs, transformation vectors and methods of the present invention, invasion of environments and contamination of commercial non-engineered productions by transgenic plants can be avoided. Methods are also taught for transformation of Brassica species.

37 Claims, 6 Drawing Sheets

SEQUENCE LISTING

```
<160> NUMBER OF SEQ ID NOS: 3

<210> SEQ ID NO 1
<211> LENGTH: 39
<212> TYPE: DNA
<213> ORGANISM: Artificial Sequence
<220> FEATURE:
<223> OTHER INFORMATION: primer

<400> SEQUENCE: 1
aaaatctaga ctgcaggtac cgcactcggt ggagatttg                              39

<210> SEQ ID NO 2
<211> LENGTH: 37
<212> TYPE: DNA
<213> ORGANISM: Artificial Sequence
<220> FEATURE:
<223> OTHER INFORMATION: primer

<400> SEQUENCE: 2
aaaaggatcc cacagcgtgt gcctaaatag gattgct                                37

<210> SEQ ID NO 3
<211> LENGTH: 32
<212> TYPE: DNA
<213> ORGANISM: Artificial Sequence
<220> FEATURE:
<223> OTHER INFORMATION: primer
<220> FEATURE:
<223> OTHER INFORMATION: primer

<400> SEQUENCE: 3
aaaatctaga gtccatggtg gccattacct cg                                     32
```

TRANSGENIC PLANTS AND METHODS FOR PRODUCTION THEREOF

CROSS-REFERENCE TO RELATED APPLICATIONS

This is a continuation of International Application No. PCT/CA99/01223, having an international filing date of Dec. 22, 1999, and which claims priority from U.S. Provisional Patent Application Serial No. 60/113,546 filed on Dec. 22, 1998, both of which are incorporated herein by reference.

FIELD OF THE INVENTION

The present invention is related to transgenic plants and, in particular, transgenic plants suitable for environmentally responsible field release and genetic constructs and vectors for production thereof. The present invention also relates to novel genetic constructs for the convenient selection and identification of transgenic plants and to progeny derived therefrom. The present invention is additionally related to novel vectors and transformation methods for production of transgenic Brassica species.

BACKGROUND ART

Transgenic Plants

It is known that new and altered traits (so-called "novel traits") can be imparted to crop species by recombinant DNA technology. In order to derive these crops with novel traits, a method to insert recombinant DNA into the crop genome is required. This method, commonly referred to as transformation, is technically challenging and requires significant effort in developing the protocols for culture, transformation itself and regeneration of whole plants. In some species transformation has become routine, while in other species transformation remains difficult and time-consuming. Nevertheless, some crop varieties that were genetically engineered to express novel traits have been released into the commercial production chain, and others are undergoing field trials in preparation for commercial release Many of these transgenic crop varieties have novel traits that provide altered phenotypes. These phenotypes include novel compositions, enhanced resistance to pests, disease or environmental stresses, and tolerance to herbicides. Such tolerance provides new means to control weeds and new production opportunities for farmers.

Many current novel traits in commerce affecting agronomic characteristics are collectively referred to as "input" traits, i.e. those traits that relate to the economics of production. For example, herbicide tolerance is an input trait as it allows farmers more options in controlling weeds; typically the costs of weed control can be lowered by these novel herbicide tolerances. Thus the economics of production or "inputs" required to grow the crop are favorably altered. Other traits such as resistance to insects can lower the costs for farmers through reduced chemical insecticide applications.

In addition to input traits, there are "output" traits that alter the composition or quality of the harvested plant. Such traits impact the final products or "outputs" from a crop and can include altered oil or meal composition, reduced anti-nutritional content and crops with altered processing characteristics. There has been a considerable effort towards the development of crops with output traits that provide new products, economic value and increased utility.

Some traits are classified as high-value "output" traits. Such traits reside in crop plants used for "molecular farming" to produce novel proteins with commercial or pharmaceutical applications. Molecular farming holds considerable promise for the economical production of large volumes of commercially useful and valuable proteins. Use of crop plants to mass produce proteins offers many advantages over fermentation technology including: ease of production; stability of the product when synthesized in plant storage organs such as tubers or seed; and possibility of recovering valuable co-products such as meal, oil or starch from the plants.

Proteins contemplated for mass production by molecular farming include industrial enzymes; for example, those derived from microbial sources such as proteases, starch or carbohydrate modifying enzymes (e.g. alpha amylase, glucose oxidase, cellulases, hemicellulases, xylanases, mannanases or pectinases). Additionally, the production of enzymes such as ligninases or peroxidases which are particularly valuable in the pulp and paper industry, has been suggested within various crop species. Other examples of commercially or industrially important enzymes which can be produced using molecular farming are phosphatases, oxidoreductases and phytases. The number of industrially valuable enzymes is large and plants offer a convenient vehicle for the mass production of these proteins at costs anticipated to be competitive with fermentation.

Additionally, molecular farming is being contemplated for use in the production and delivery of vaccines, antibodies (Hein, M. B. and Hiatt, A. C., U.S. Pat. No. 5,202,422), peptide hormones (Vandekerckhove, J. S., U.S. Pat. No. 5,487,991), blood factors and the like. It has been postulated that edible plants which have been engineered to produce selected therapeutic agents could provide a means for drug delivery which is cost effective and particularly suited for the administration of therapeutic agents in rural or underdeveloped countries. The plant material containing the therapeutic agents could be cultivated and incorporated into the diet (Lam, D. M., and Arntzen, C. J., U.S. Pat. No. 5,484,719).

In total, the novel input and output traits contemplated for crop plants are very broad in scope and can lead to the development of numerous new products and processes. Accordingly, reliable means to produce plants with novel traits and incorporate the initial transgenic plants into breeding and variety development programs are important tools for the delivery of these products into commerce.

A problem of transgenic plant production is that upon recovery of a transgenic event in a plant cell, a considerable effort is needed to recover morphologically normal, fertile plants for use in subsequent breeding schemes. Thus methods that allow for the simple identification of plants that have received the transgene is a primary objective for commercialization.

The selection or identification of transgenic plants by reliable methods that do not require biochemical or calorimetric assays are particularly convenient. A method that allows for flexibility can be additionally valuable, such as a scheme that can be used at any point in the development of a transgenic variety. A most preferred method would allow selection in culture, identification in breeding and introgression activities, as well as identification and discrimination at the field level.

Concerns Associated with Field Release of Transgenic Plants

It has been suggested that the release of genetically modified crops could lead to environmental damage because of their expression of genetic potential that would not ordinarily be attained by natural selection or via sexual recombination. It has further been suggested that released transgenic plants could invade natural ecosystems either through the spread of the plants themselves or through hybridization with wild relatives. These issues have been extensively debated and experimentation has been initiated to test for continued survival of transgenic plants and transfer of traits from crop species to wild relatives. (e.g. University of California, *Risk assessment in agricultural biology: proceedings of an international conference,* 1990, Casper, R., & Landsman, J., 1992; The bio-safety results of field tests of genetically modified plants and microorganisms. *Proceedings of the 2nd International Symposium on The Biosafety Results of Field Tests of Genetically Modified Plants and Microorganisms,* 1992, Goslar, Germany, Dale, P. et al., 1992; The field release of transgenic plants, The British Crop Protection Council. *Brighton Crop Protection Conference: Pests and Diseases,* Vols. I, II and III; *Proceedings of the 3rd International Symposium on The Bio-Safety Results of Field Tests of Genetically Modified Plants and Microorganisms,* 1994, Monterey, Calif., Jones, D. D., 1994)

The consensus of the studies and experimental results achieved to date supports the view that the degree of potential spread of transgenes to wild relatives is highly dependent upon the species and environmental conditions. Crossing with relatives is not likely with some species and probable for others (Raybould & Grey, J., *Applied Ecology* 30: 199–219, 1993). The degree to which any transformed plant can be invasive of other habitats, and hence the environmental risk, is also dependent on the plant species itself. Many crops are highly specialized and adapted to non-competitive cultivation practices and, thus, they are not generally considered a serious environmental risk (Dale et al., *Plant Breeding* 111:1–22, 1993; Fishlock, D., *The PROSAMO Report,* published by the Laboratory of the Government Chemist, Queens Road, Teddington, Middlesex, UK TW11 OLY).

However, it is generally agreed that there are probably some risks that certain crop plants, ornamentals or plants cultivated for natural pharmacological purposes could become weedy pests since many of the weedy species currently affecting agricultural production were at one time introduced from another environment, frequently for ornamental, culinary or medicinal reasons (Keeler, K. H., *Biotechnology* 7: 1134–1139, 1989).

While years of study will be required to understand fully the potential impact of transgenic plants on the environment, a potentially more serious near term problem relates to contamination of agricultural production with novel traits from transgenic plants. Both Xenia effects (direct effect of cross pollen on the composition of seed) and volunteers or seed that remain in the field can contaminate subsequent agricultural production. Although such events have not been a major problem in the past, the inadvertent contamination of crops intended for general consumption with visually indistinguishable varieties developed for other purposes, for example, crops that contain a pharmaceutically active protein, has become an issue of particular concern. Accordingly, the ability to discriminate transgenic crops in a simple and reliable way is of value.

Currently, physical isolation combined with border rows that function as pollen traps have been employed to contain plants with transgenic traits under study and development (e.g., Agriculture and Agri-Food Canada, Regulatory Directive 94–08; *Assessment Criteria for Determining Environmental Safety of Plants with Novel Traits,* Regulatory Directive 94–09: *The Biology of Brassica napus L. (Canola/Rapeseed),* Regulatory Directive 95–01; *Field Testing Plants with Novel Traits in Canada*). However, with increasing commercial production of transgenic plants, the potential for contamination within a commodity increases dramatically. This potential contamination has become a major concern for the oilseed rape industry and will become a significant issue for other major crops (e.g. corn), as greater numbers of different recombinant genotypes reach the market place.

Contamination of commercial crop production with traits from another cultivar that affect quality and performance is a potentially serious problem. However, because of possible contamination of food products, a potentially more serious problem is the use of canola (or other crops) as a production vehicle for heterologous proteins of commercial or medicinal value. Although production standards as set out above can be implemented to preserve the identity of individual transgenic lines and reduce unintended contamination, the outflow of genes to other cultivars may eventually occur. The issues relating to the occurrence and spread of genes that do not impart a distinctive morphology or an easily identifiable trait (such as herbicide tolerance) have not yet been resolved.

Though many techniques have been used to introduce genes into plants, genetic constructs in the prior art do not include features that are useful for identifying and selecting transgenic plant cells in culture or for controlling the persistence or potential spread of the transgenes. Accordingly, genetic constructs that operate within a mechanism that permits discrimination of transgenic plants from non-transgenic plants, or discrimination among transgenic plants carrying different traits, would solve the contamination problem. A mechanism that has no effect on non-transgenic plants, yet allows the plants containing a specific transgene to be eliminated as they are identified, would also provide a solution. Furthermore, a mechanism which selectively removes crop plants containing specific transgenes from other commercial crops not having those transgenes would also be valuable.

Methods for Transformation of Plants

In general, two methods for introducing DNA into plant cells are currently in widespread use. The first involves the use of Agrobacterium, or similar soil bacteria, to transfer DNA. Target plant tissues or cells are co-cultivated with a suitable Agrobacterium strain that injects plasmid DNA into plant cells (Schilperoot, R. A. et al., U.S. Pat. No. 4,940,838; Schilperoot, R. A. and Hoekema, A., U.S. Pat. No. 5,464,763). Subsequently, the individual transformed plant cells are regenerated into whole plants.

The Agrobacterium transformation system is based historically on the use of a natural bacterial vector that is the causal agent of crown gall disease. Crown gall disease represents the results of a natural form of plant transformation. The naturally occurring tumor inducing (Ti) plasmids of Agrobacteria comprise: the DNA sequences needed for the transfer of DNA into plant cells; the DNA sequences needed for integration of foreign DNA into the host plant DNA, called the border fragments; and genes, called oncogenes, that result in the formation of plant growth regulatory substances that cause the formation of galls at the site of infection. The Ti plasmids also typically code for genes that result in the formation of certain types of unusual amino acids (opines) that can be metabolized by Agrobacteria, but not by plant cells. In the natural system, the portion of the Ti plasmid which is transferred to the recipient plant host (the T-DNA) usually contains all these genes and DNA sequences.

The oncogenes of the tumorigenic Agrobacterium strains have been extensively studied. Generally, there are two types of oncogenes on the Agrobacterium plasmid: the tmr oncogene and the tms oncogenes. The tmr oncogene (also known as the ipt gene) encodes an enzyme which synthesizes isopentyl-adenosine 5'-monophosphate which is a cytokinin plant hormone that induces shoot formation in a suitable host. The oncogenes referred to as tms (comprising tms oncogene 1 and tms oncogene 2) encode enzymes responsible for auxin overproduction in suitable hosts, leading to the production of roots. When combined, the tms and tmr genes usually lead to the production of crown galls on suitable hosts.

Plants which contain the Ti oncogenes are phenotypically abnormal, having crown gall tumors or curled and twisted leafs due to growth hormone imbalance. These abnormal plants are unsuitable for commercial applications. Although these plants can be easily identified following transformation, they do not form morphologically normal plants. Accordingly, the Agrobacterium Ti plasmid has been modified in a variety of ways, and typically by removal of the oncogenes, to become a tool for the introduction of DNA into plant cells. Generally, Agrobacterium transformation methods that have been used to date have used Ti plasmids in which the genes that result in the formation of cytokinins and auxins and the genes for opine synthesis have been removed. Such plasmids are generally referred to as being "disarmed". Accordingly, an "armed" Ti plasmid is generally considered to contain an oncogene.

The Ti plasmid for use in plant transformation has further been engineered to contain restriction sites, for the convenient introduction of foreign genes between or adjacent to one or more of the border fragments, and genes for identification and selection of transformed cells, such as antibiotic resistance genes or β-glucuronidase synthase (GUS) genes. Replication genes are often introduced to the Ti plasmid to allow replication of the plasmid in non-Agrobacterial hosts. The vir (virulence) genes that are required for the mobilization of DNA and transfer of the plasmid from the bacterial cell are often retained on a separate plasmid or in a location of the Ti plasmid distinct from that containing the DNA which is to be transferred and, as such, are not transferred to the recipient plant cells.

The second wide spread technology employed to generate transformed plants involves the use of targeted microprojectiles. These methods have been employed to transform both monocots and dicots that are recalcitrant to Agrobacterium methods. A variety of different microprojectiles and methods of bombardment have been described in, for example, Sanford, et al., U.S. Pat. No. 4,945,050; McCabe, et al., U.S. Pat. No. 5,149,655; Fitzpatrick-McElligott et al., U.S. Pat. No. 5,466,587; and Coffee et al., U.S. Pat. No. 5,302,523, U.S. Pat. No. 5,464,765. The DNA introduced using targeted microprojectiles comprises similar functional features for expression in plant cells, equivalent to those introduced via Agrobacterium systems, for example, the vector used often comprises engineered sites for foreign gene insertion and genes needed for identification or selection of transformants.

Other methods that have been used to obtain transformed plants include: microinjection directly into cell nuclei (Crossway et al., U.S. Pat. No. 4,743,548); and direct DNA uptake by protoplasts (Paszkowski et al., U.S. Pat. No. 5,231,019, U.S. Pat. No. 5,453,367).

Although the general approach to plant transformation is well-understood, the practical application of plant transformation processes is often limited by genotypic response of plant cells to transformation and culture conditions. It is not unusual for only one or two narrow genotypes within a species to be amenable to transformation. Accordingly it is not simple, or in some cases possible, to efficiently transform all genotypes within a crop species. Despite numerous attempts to alter culture and transformation protocols, some plant genotypes are recalcitrant to transformation by techniques that are efficient within other genotypes. Thus in many cases a specific genotype that is amenable to transformation is first used, then the transgenic event is crossed, or "introgressed" into germplasm that is recalcitrant to the same transformation method. Although this method may allow for the eventual introduction of a transgene into a line that can not be transformed without undue effort, the process takes time and effort since one has to select for the transgene at every sexual cross.

Thus a method that allows rapid discrimination of plants into which the transgene has been introduced by either transformation or introgression, would greatly facilitate production of transgenic plants. In particular, a non-destructive visual assay would allow rapid screening of large numbers of breeding lines and segregating populations. This screening process, if applied at the seedling stage or even at the stage of seed development (e.g. embryo rescue), would find utility within commercial varietal production programs by allowing selection of lines at an early stage, thus eliminating the need to grow plants to maturity, thereby saving time and land resources. Such a method could also be used to eliminate significant number of null lines from cultivation and allow for a streamlined breeding and introgression process. In particular, such a method would be useful for producing Brassica plants carrying transgenes for input or output traits, including high value output traits.

Brassica Transformation

Transformation of members of the Cruciferae family by Agrobacterium and other methods has been reported. However, many of the reports that relate specifically to Brassica transformation have detailed the difficulty in routinely obtaining transformed Brassica species by Agrobacterium mediated transformation. Many of the reports have shown success with one or two particular varieties, but there is no teaching of detailed methods that are generally applicable to all species within the Brassica genus. Although many manipulations of culture conditions can be employed, some varieties have proven to be extremely difficult to transform by previously reported methods. Thus significant effort is expended for the introduction of transgenes in these genotypes by crossing and introgression. Any improvements and discoveries that allow for the reliable generation of transgenic plants from these genotypes or allow for a more efficient means to introgress these traits would be a significant improvement over the art.

Many of the initial Brassica transformation studies were carried out with a single genotype, *B. napus* cv Westar (Radke et al, *Theor. Appl. Genet.* 75:685–694, 1988; Moloney et al., *Plant Cell Reports* 8:238–242, 1989; Moloney et al., 1989, U.S. Pat. No. 5,188,958; Moloney et al., 1989, U.S. Pat. No. 5,463,174). Westar was a convenient choice since it responded to tissue culture and transformation protocols described in the references cited above and allowed recovery of transgenic plants. Westar remains the genotype of choice for transformation experiments; however, the agronomic properties of the variety are considered poor by comparison with recent cultivars. Hence a gap remains in reliable transformation technology and commercial genotypes of *Brassica napus* oilseed.

Moreover, many Brassica transformation studies conducted using the described methods, or variations thereof, have produced results that are highly variable and are dependent upon the innate response of the specific plant materials to the transformation protocol. As an example, the transformation frequencies that have been achieved for *Brassica napus* are sometimes variable and very low (Fry et al., *Plant Cell Reports* 6:321–325, 1987; Mehra-Palta et al., *In Proc 8th Int. Rapeseed Congress,* Saskatoon, Saskatchewan, 1991; Swanson and Erickson, *Theor. Appl. Genet.* 78:831–835, 1989). Variable and often low transformation frequencies have also been observed with other Brassica species, such as *B. oleracea* (Christie and Earle, *In Proc 5th Crucifer Genetics Workshop,* Davis, pp 46–47, 1989; Metz et al., *Plant Cell Reports* 15: 287–292, 1995; Eimert and Siegemund, *Plant Molec. Biol.* 19:485–490, 1992; DeBlock et al., *Plant Physiol.* 91:694–701, 1989; Berthomieu and Jouanin, *Plant Cell Reports* 11:334–338; Toriyama et al, *Theor. Appl. Genet.* 81:769–776, 1991); *B. rapa* (Radke et al., *Plant Cell Reports* 11:499–505, 1992; Mukhopadhyay et al., *Plant Cell Reports* 11:506–513, 1992); *B. juncea* (Barfield and Pua, *Plant Cell Reports* 10:308–314, 1991; Deepak et al., *Plant Cell Reports* 12:462–467, 1993; Pua and Lee, *Planta* 196:69–76, 1995); *B. nigra* (Gupta et al, *Plant Cell Reports* 12:418–421, 1993); and *B. carinata* (Narasimhulu et al., *Plant Cell Reports* 11:359–362, 1992; Babic, M. Sc. Thesis, Univ of Saskatchewan, 1994).

The many Brassica species, varieties and cultivars represent a very diverse group with radically different morphologies and physiological characteristics. Many Brassica species of commercial interest do not respond well or at all to the methods previously described. In particular, *Brassica napus* oilseed species with unusual fatty acid compositions appear to be recalcitrant to conventional transformation efforts. One genotype, typified by the variety AG019, as described in U.S. Pat. No. 5,965,755 is a high oleic acid, low linoleic acid genotype that is unresponsive to conventional transformation methods, for example, that described by Moloney (ibid). The variety AG019 and varieties derived therefrom have valuable fatty acid compositions that provide oil with improved oxidative stability and nutritional value. Crossing with a conventional oil profile *Brassica napus,* for example, a transformed Westar, as a means to introduce a transgene, causes a loss in oil profile and requires significant breeding efforts to reconstruct the desired oil profile. In most cases it is uncertain that this can be attained. Thus, a transformation method is required which is useful for transformation of recalcitrant Brassica, particularly *Brassica napus* oilseed species with altered oil profiles, more particularly transformation of Brassica species AG019 and progeny derived therefrom.

Accordingly, methods to transform recalcitrant genotypes of Brassica will be valuable. Furthermore, methods to identify transformed plant cells, and plants and progeny derived therefrom will also be valuable particularly if the methods are simple, non-destructive in nature and allow visual identification of the plants or cells that contain the transgene of interest. If such methods further provide discrimination at the field level, then a wide range of appliations is feasible.

Methods have been developed that address these needs to some degree. Visual marker genes such as the β-Glucuronidase or GUS gene are available, but require a biochemical or histochemical assay. Genes which respond to applied chemicals are typified by so-called "conditionally lethal" genes. However, these typically lead to a lethal phenotype, hence are not useful for tracking transgenes in a breeding process. Accordingly, it is an object of the present invention to provide a conditionally lethal gene that is useful in a breeding program, as well as other commercially important objectives.

Conditionally Lethal Genes

Conditionally lethal traits and genes which impart these traits, are known. Many conditionally lethal genes lead to a lethal phenotype and plant death. However, some conditionally lethal genes can be used in a fashion that will not necessarily lead to cellular death. An example of such a conditionally lethal gene is the Agrobacterium Ti plasmid tms oncogene 2. This oncogene codes for the enzyme indoleacetamide hydrolase (IAMH) that, in combination with Agrobacterium oncogene 1 which codes for indoleacetamide synthase (IAMS), forms part of the indoleacetic acid (IAA) synthesis pathway typical of this type of bacterium.

The formation of indoleacetic acid by plants takes place by a different pathway from that of Agrobacterium. Hence, the expression of IAMH (oncogene 2) in plants does not result in the formation of indoleacetic acid because the substrate for the enzyme, indoleacetamide, is not present in plant cells. However, application of indoleacetamide to plants expressing the IAMH gene results in the rapid accumulation of IAA. Even though IAA is a naturally occurring auxin plant growth regulator, uncontrolled high levels of IAA rapidly disturb cellular metabolism resulting in senescence and cell death. The enzyme IAMH is capable of hydrolyzing other indoleamide-related substrates including naphthalene acetamide resulting in production of the well known synthetic plant growth regulator naphthalene acetic acid (NAA).

The use of a conditionally lethal gene, such as the IAMH oncogene, for roguing maize plants is described in U.S. Pat. No. 5,180,873 (Jorgensen) issued January, 1994. Jorgensen teaches transformation of plants to contain a conditionally lethal gene. The plants are subsequently subjected to linkage analysis, then selected for close linkage between the lethal gene and a target locus which is either pre-existing or introduced by traditional breeding techniques. U.S. Pat. No. 5,426,041 of Fabijanski et al issued June 1995, teaches a method of hybrid seed production using IAMS in combination with IAMH. Neither patent teaches a method for using the oncogene 2 in a non-lethal means or for selection during and after transformation. Neither patent teaches a method for using oncogene 2 for selectively removing related species having acquired the transformed genetic material.

Thus a conditionally lethal gene within a genetic construct also containing a novel trait offers a convenient means to control spread of the novel trait. However, because the lethal gene does not provide a non-destructive means to identify or select transformed plant cells, specifically Brassica cells, traditional conditionally lethal genes do not solve the present problem of selecting, identifying and tracking transgenic plants and progeny derived therefrom.

Accordingly, another object of the present invention is to modify and use a previously identified conditionally lethal gene to track transgenes during the breeding and commercialization process as well as under field conditions.

SUMMARY OF THE INVENTION

The present invention provides methods and genetic constructs for the production of transgenic plants that can be identified visually and non-destructively. The present invention further provides transgenic plants that can be safely and specifically removed from a growing site by application of a benign chemical that is converted to a phytotoxic agent in the presence of the expressed genetic construct. The methods, genetic constructs and plants of the present invention are particularly suited for those applications related to input or output traits or the heterologous production of proteins.

The present invention provides a genetic construct comprising a conditionally lethal gene operably associated with a promoter functional in a plant cell. The gene is used to select, identify or selectively kill a plant expressing said gene.

The present invention also provides a genetic construct comprising two genes adapted for expression in a plant cell. One gene is a conditionally lethal gene. Either or both gene is operably associated with a promoter functional in a plant cell.

The genetic construct comprises a conditionally lethal gene expressed to kill the plant in response to an applied chemical formulation. Therefore, in accordance with a broad aspect of the present invention, there is provided a genetic construct comprising: a) a conditionally lethal gene adapted for expression in a plant cell and b) a novel trait gene coding for a protein, peptide or antisense RNA; the novel trait gene being adapted for expression in a plant cell and, when expressed, producing a desired phenotype.

In accordance with another broad aspect of the present invention, there is provided a method for producing a recombinant plant which can be identified, comprising: a) transforming a plant cell with a genetic construct including a novel trait gene and a conditionally lethal gene, the novel trait gene and the conditionally lethal gene being adapted for independent expression in the plant; and b) regenerating the plant cell to a whole plant.

In accordance with another broad aspect of the present invention, there is provided a method for the visual identification of a plant or progeny therefrom containing a conditionally lethal transgene, comprising: (a) treating the plant or population of plants with a formulation comprising a benign chemical that is a substrate of the product of the conditionally lethal gene (the benign chemical being applied at a level which, upon conversion to a phytotoxin by the product of the conditionally lethal gene, results in a sub-lethal level of the phytotoxin); (b) visually identifying plants which manifest the sub-lethal phenotype; and (c) selecting the identified plants and allowing their recovery into normal plants.

The present invention also provides a method for visual identification of a germinating seed or plant embryo comprising oncogene 2 as a transgene, comprising: (a) culturing the seed or embryo on a medium containing an indoleamide or a related derivative optionally containing an auxin transport inhibitor; and (b) visually identifying the germinated seed or embryo which manifests the phenotype.

The present invention also provides a method for selecting a germinating seed or plant embryo comprising oncogene 2 as a transgene, comprising: (a) culturing the seed or embryo on a medium containing an indoleamide or a related derivative, optionally containing an auxin transport inhibitor; (b) visually identifying the germinated seed or embryo which manifest the phenotype; and, (c) transferring the identified seed or embryo to a medium without indoleamide or auxin transport inhibitor; thereby obtaining the germinating seed or plant embryo comprising oncogene 2 as a transgene.

In accordance with another aspect of the invention a method is provided for selecting transgenic Brassica plant cells during transformation, comprising: transformation of a Brassica plant cell with a genetic construct comprising an oncogene and optionally, a gene encoding a novel trait; exposing said plant cells to a benign auxin derivative of a plant hormone capable of being acted upon by said oncogene at one step in the culture process; culturing the cells and using the conversion of the benign derivative into an active plant hormone as a means to identify said transformed plant cells which manifests the phenotype associated with the active hormone; and recovering transformed plant cells.

The invention also provides a method for transforming *Brassica napus,* comprising inclusion of naphthalene acetic acid in the media at the callusing and recovery step.

The invention is well suited to the production of crop plants, such as Brassica species/varieties, for large scale agricultural and industrial applications. The method finds utility for the tracking and identification of transgenes during the breeding process. The method also finds utility for the production of commercial plant varieties comprising novel traits wherein the contamination of other commercial productions of the same species, via cross pollination or volunteer seed, must be avoided. Additionally, the invention provides for environmental protection by providing a method of selectively removing from any environment plants having transgenes.

The present invention specifically provides a method to produce crop plants which express heterologous proteins. The method of the invention can be used to substantially eliminate contamination of heterologous protein expressors from other commercial productions.

In addition, the present invention provides methods for transforming Brassica species and varieties including those found previously to be recalcitrant or transformable only at very low efficiencies. This includes the commercially important high oleic/low linoleic varieties, particularly AG019 and progeny derived therefrom.

BRIEF DESCRIPTION OF THE DRAWINGS

In the Figures, "C.R." refers to "coding region"; "TER." refers to "termination region"; "PROM." refers to "promoter", and "PR" refers to "primer".

DESCRIPTION OF THE SPECIFIC EMBODIMENTS

Figure 1:
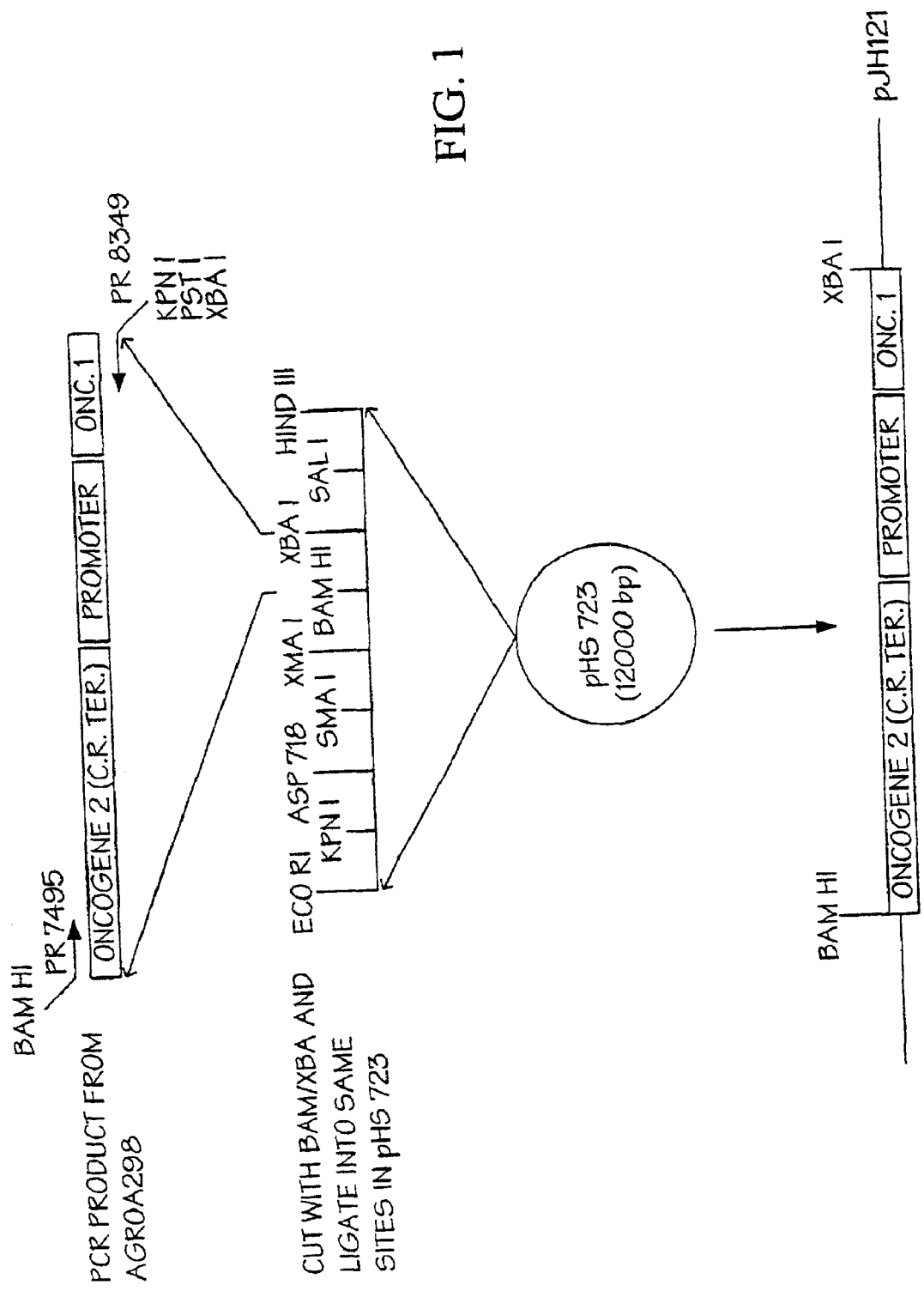
FIG. 1 illustrates the construction of the plant transformation vector pJH121 comprising the conditionally lethal Agrobacterium oncogene 2 in the vector pHS723. In addition to the oncogene, the vector contains a gene coding for the beta glucuronidase—kanamycin resistance fusion protein for the selection of plant cells.

The invention provides genetic constructs for producing transgenic plants that can be easily identified visually. Said genetic constructs also provide for recombinant plants that can be removed easily from any growing location by the application of a chemical formulation that affects solely those transgenic plants. The genetic constructs also provide a novel selection method that can be used during the transformation process.

According to a preferred embodiment, the genetic construct contains a conditionally lethal gene and a second gene coding for a desired trait. Either or both genes may be modified so that they can be expressed in a plant cell.

It is desirable that the genetic construct be so constructed that the DNA sequences comprising the transcriptional and translational regulatory regions and the DNA encoding both the target and conditionally lethal genes be linked by multiple cloning sites to allow for the convenient substitution of alternative or additional target and/or conditionally lethal DNA sequences.

The genetic construct of the present invention can be introduced to a vector for transformation of plants. The vector comprises the conditionally lethal gene adapted for selective expression in plants linked to the target gene also adapted for expression in plants.

The vector can comprise the genetic sequences required, for example, for replication, transformation and selection in plants, as are known. For example, the vector can include the right and optionally, the left T-DNA borders, where the vector is to be used in an Agrobacterium-mediated transformation system, or a kanamycin resistant gene (NPTII) for selection of transformants.

The genetic construct can be introduced to plane cells to form recombinant cells by any suitable method, such as, for example, Agrobacterium mediated, electroporation, or particle gun methods. The plant cells can be regenerated to whole plants by any suitable method. The recombinant plants can be used in plant breeding or directly in agricultural production.

The second gene of the construct encodes a desired protein, peptide or antisense RNA. The gene can be, for example, part or all of a naturally occurring gene from any source (i.e. a heterologous gene), altered form of a naturally occurring gene, a synthetic DNA sequence or a combination of naturally occurring and synthetic sequences. One or more introns can be present within the coding sequence of the target product. This second gene is capable of being transcribed or expressed as a translation product in a plant system; for example, by having appropriate transcription and translation initiation and termination regions. The expression of this second gene can be regulated by, for example, an unaltered or altered native, a constitutive, an inducible, a developmentally regulated or tissue specific promoter that can be the same as or different from the promoter regulating expression of the conditionally lethal phenotype. The choice of promoter for the gene will vary depending on the desired effect or result which is to be achieved.

In molecular farming applications, seed specific expression of the second gene is particularly useful. Thus, the second gene in these systems preferably includes transcriptional and translational regulatory regions capable of expression in developing plant seeds, and more specifically, in the seed embryo or other seed tissue capable of triglyceride storage. Such regulatory regions can include, for example, the oleosin promoter (Plant et al., *Plant Molecular Biology* 25: 193–205, 1994). Preferably, the second gene comprises: (i) transcription and translation regulatory regions functional in plants, including initiation and termination regions; and (ii) a region which encodes a chimeric peptide or protein. This coding region preferably comprises (a) a region which codes for at least a portion of an oil-body specific protein sufficient to provide targeting or partitioning of the chimeric product to an oil body and, (b) the region coding for the desired protein or trait. The oil-body region of the chimeric gene may include an oil-body specific promoter. The chimeric peptide or protein can also comprise a peptide sequence which links the oil-body specific protein to the desired protein and which can be specifically cleaved by chemical or enzymatic means (Moloney, PCT/CA92/00161).

The present invention provides a method for preparing a transgenic plant which can be selectively removed from a growing environment. A genetic construct is provided which includes a conditionally lethal gene and a second gene which codes for a desired trait. A plant cell is transformed with the genetic construct and regenerated into a whole plant. Preparation of the genetic construct, transformation and regeneration are carried out using any suitable procedures.

Specifically the present invention provides for the production of plants containing a transgene comprising an input or output trait or any desired trait, with the added novel feature that such transgenic plants and progeny therefrom can be removed specifically from a growing site, when desired. The invention uses a genetic construct which includes (a) a novel trait gene to which is linked, (b) a gene that codes for a product which is capable of converting a benign substance to a substance which causes phenotypic change or death of the entire plant. The genes identified as (b) are termed herein as conditionally lethal genes.

According to another embodiment, the genetic construct comprises a conditional lethal gene operably associated with a promoter functional in a plant cell. In this instance the conditional lethal gene is used to select, identify or selectively kill a plant that expresses it.

Conditionally lethal genes can be obtained from any source such as, for example, plant, bacterial, viral, or animal systems, and can be wild-type, altered or synthetic. These genes are adapted for transcription and translation in a plant system and include, for example, any necessary transcription and translation initiation and stop sequences. The conditionally lethal gene can be regulated to initiate cell death for example in response to application of a chemical substance or in response to application of a physiological stress, such as heat and/or cold shock. In one embodiment, a conditionally lethal gene is used which is activated to cause cell death by application of a substance which has no known adverse effects on the growing environment.

Many conditionally lethal genes are known in the art. Conditionally lethal genes typically have two mechanisms of action. The lethal phenotype is conditional upon either the presence of a non-toxic substance or the induction of gene activity. In the first instance a gene expresses a product capable of acting upon a non-toxic substance, which is usually applied externally, causing it to become toxic and capable of killing a plant cell. In this instance the conditionally lethal phenotype is dependent on the presence of the non-toxic substance. In the absence of the non-toxic substance the lethal phenotype is not expressed; in the presence of the substance the lethal phenotype is observed.

In the second instance, a conditionally lethal gene encodes a product that is directly toxic to a plant cell. However, expression of the toxin gene is regulated by a promoter so that expression of the toxin can be repressed when desired and allow the plant to grow. In this instance, the lethal phenotype is observed when the promoter is induced to express. No application of an external substance is required.

In addition to the genes described below, a person skilled in the art can readily assay a candidate gene for lethality in plants. Moreover, the gene may be assayed to see if it can be used on its own or whether a regulatable, possibly heterologous, promoter is required to induce a conditional lethal phenotype.

Examples of conditionally lethal genes useful in the present invention and applications for molecular farming are, but are not limited to: an oncogene, such as oncogene 4 encoding the enzyme isopentyltransferase which causes overproduction of cytokinin, having a chemically inducible promoter such as, for example, the promoter from the glutathione-S-transferase II gene inducible by N,N-diallyl 2,2-dichloroacetamide and related compounds (WO9301294; Albertsen, M. C. et al., U.S. Pat. No. 5,478, 369); or an oncogene under the control of a cold inducible promoter such as, for example, the low temperature induced genes from Arabidopsis (Baker et al., *Plant Molecular Biology* 24: 701–713, 1994; Lang and Pulva, *Plant Molecular Biology,* 20: 951–962, 1992; Nordin et al., *Plant Molecular Biology* 21: 641–653, 1993) or Brassica (White et al, *Plant Physiology* 106: 917–928, 1994). Other useful conditionally lethal genes are those that convert a non-toxic substance to a toxic substance, for example, the genes for: the enzyme methoxinine dehydrogenase which converts 2-amino-4-methoxybutanoic acid (methoxinine) to toxic methoxyvinyl glycine (Margraff, R., et al., *Experimentia* 36: 846, 1980); the enzyme rhizobitoxine synthase that converts non-toxic methoxinine to toxic 2-amino-4-[2-amino-3-hydroxypropyl]-trans-3-butanoic acid (rhizobitoxine) (Owens, L. D., et al., *Weed Science* 21: 63–66, 1973); and the enzyme phosphonate monoester hydrolase capable of hydrolyzing non-toxic derivatives of the herbicide glyphosate to the phytotoxic glyphosate compound (Dotson, S. B. and Kishore, G. M., U.S. Pat. No. 5,254,801).

Conditionally lethal gene products which act on substances not normally found in plants can be regulated by one or more of: their native promoter, an inducible promoter or a constitutive promoter. Conditionally lethal gene products which act on substances normally found in plants should preferably be regulated by inducible promoters so that they will only be active under certain conditions, as determined by the action of the promoter to be lethal to a plant. Many inducible promoters are known as are screening procedures for identification of suitable promoters. The useful promoter can be active in all or specific cell types and/or be developmentally regulated. Many different types of cell or tissue specific and developmentally regulated promoters have been described in the literature (e.g. Rocha-Sosa et al., U.S. Pat. No. 5,436,393; Allen and Lonsdale, U.S. Pat. No. 5,412,085; No. 5,391,725; Coruzzi et al, U.S. Pat. No. 5,391,725; Conklin and Yamamoto, U.S. Pat. No. 5,459,252) and those appropriate to the trait of commercial interest can be selected and used in the practice of the present invention. However, it is to be understood that any promoter that provides sufficient levels of expression to cause cell death in the transformed plant is suitable for use in the present invention. Promoters that provide high levels of expression either during extended periods of time or when and where required are preferred.

Accordingly, in a specific embodiment of the present method, a conditionally lethal gene is linked to a gene encoding a heterologous protein capable of being expressed in a plant cell. Said conditionally lethal gene being capable of expressing a lethal phenotype under exposure to a specific chemical formulation of stress.

A preferred conditionally lethal gene is oncogene 2 from the Ti plasmid of *Agrobacterium tumefaciens* that encodes the enzyme indoleacetamide hydrolase (IAMH). As an example, the DNA sequence of the octopine T-DNA, including the coding region and promoter sequence of oncogene 2, is disclosed in U.S. Pat. No. 5,428,147 of Barker et al. The substrate for IAMH includes various indoleamides and related auxin derivatives, including the synthetic chemical napthalene acetamide (NAM). Application of NAM to plant cells expressing oncogene 2 causes production of the phytotoxic agent napthalene acetic acid (NAA). The DNA encoding the conditionally lethal gene also comprises a promoter from which IAMH is expressed in plant cells in sufficient quantities to confer the conditionally lethal phenotype. Said promoter can be the promoter native to oncogene 2, a constitutive promoter, such as the Cauliflower Mosaic Virus Promoter CaMV35S, or a cell or tissue specific promoter.

In a most preferred embodiment of the present invention, the oncogene 2 of Agrobacterium is used as part of the plant transformation vector. Presence of the oncogene 2 in the plant transformation vector provides many advantages. These include: the ability to use sub-lethal doses of auxin indoleamides and related auxin derivatives to cause a visual change in phenotype in plants comprising the transformation vector; the ability to use indoleamides and related auxin derivatives for the selection of plant cells during the transformation process; and the use of the oncogene 2 as a component of seed and embryo rescue methods that allow for the identification of transgenic plants comprising the transformation vector.

The invention further provides for plants or cells transformed with the fore-mentioned constructs or vectors. In a preferred embodiment, the plant or cell is Brassica. A particular embodiment is Brassica which has an altered oil composition. Preferably the Brassica is one which has high oleic and low linoleic acid content such as AG019 or its relatives and derivatives.

In one aspect of the invention, conditionally lethal genes is valuable for controlling the spread of novel genes, including those used in molecular farming.

In one embodiment, a transgenic plant containing a conditionally lethal gene, such as the oncogene 2, is removed from a growing environment by application of a chemical agent which is converted to a phytotoxic agent in the presence of the product of the conditionally lethal gene. The chemical agent is applied at a level which results in a lethal level of the phytotoxin. In a specific embodiment, the oncogene 2 is used as the conditionally lethal gene. The gene product in this instance is IAMH, which converts an indoleamide or a related derivative to the phytotoxin NAA. In a specific preferred embodiment, the indoleamide is NAM.

In a preferred embodiment, the present invention provides the conditionally lethal gene such as the oncogene 2 as a visual, scorable marker that allows the discrimination of transgenic from non-transgenic plants. The method involves the application of a quantity of a chemical agent which, upon being converted by the expressed conditionally lethal gene, results in a sub-lethal level of phytotoxin. Plants containing the conditionally lethal transgene are identified visually as those manifesting the sub-lethal phenotype.

The invention further provides a method for selecting for the transgenic plant, since the plants identified as transgenic recover into normal plants in the absence of the chemical agent. As described above, when oncogene 2 is used as the conditionally lethal gene, the chemical agent is an indoleamide or a related derivative. In a specific preferred embodiment, the indoleamide is NAM.

Use of a conditionally lethal gene such as oncogene 2 as a visual marker allows any desired gene, including those encoding a heterologous protein or an "input" or "output" trait, to be incorporated into a plant, even when such a plant is recalcitrant to transformation, e.g. certain Brassicas such as A019.

Sexual crossing followed by visual inspection of progeny at an early stage of development provides a convenient, non-destructive, non-biochemical means to identify the transgenic plant. Literally thousands of plants can be screened at once. This method provides an inexpensive and accurate means to track the introgression of novel traits within large breeding population. No biochemical assays, such as GUS assays or nucleic acid analysis such as PCR are required. Inclusion of a conditional lethal gene, such as the oncogene 2, in plant transformation vectors that contain genes coding for input or output traits therefore allows for rapid introgression of said traits into numerous plant varieties.

A simple procedure is provided to screen for transgenic plants expressing the oncogene 2. Plant populations are sprayed with the formulated mixture of napthalene acetamide. Within 24 hours epinasty and obvious visual phenotypic changes are observed in transgenic plants. Plants without the oncogene 2 are unaffected. Plants which have been affected are selected. These recover within 72 hours and continue to grow and set seed. This phenotypic response is transmitted to subsequent generations.

The present invention further provides the oncogene 2 as a visual, scorable marker that allows the selection of germinating seeds or plant embryos that express oncogene 2. The method involves culturing the seed or embryo on a medium containing (a) an indoleamide or a related derivative,and (b) an auxin transport inhibitor; then visually identifying the germinated seed or embryo which manifest the phenotype. The identified transgenic seed or embryo is readily recovered by transferring to a medium without indoleamide or auxin transport inhibitor.

The present invention further provides a method for selecting a transgenic plant cell during transformation. The procedure uses an oncogene as part of an expression construct or vector used to transform the cell. Once the vector has penetrated the plant cell, the cell is exposed to a formula containing (a) a benign derivative of a plant hormone which becomes an active hormone in the presence of the oncogene expression product and, (b) an auxin transport inhibitor. After the cells are allowed to grow into a clump, the cell clump is identified visually as that which manifests the phenotype associated with the active hormone. The identified group of cells is then allowed to recover in the absence of the hormone derivative, and regenerated in the usual manner to a whole plant. If the oncogene is oncogene 2, then the preferred benign derivative is an indoleamide or a related derivative such as NAM and the preferred inhibitor is naphthylphthalamic acid.

Application of an auxin transport inhibitor in addition to NAM, which is converted by IAMH to NAA, greatly potentiates the effect of NAA. Thus, transgenic plant cells comprising a desired trait and the oncogene 2 are identified by application of a formulation that includes: (a) an indoleacetamide and related compounds, and (2) an auxin transport inhibitor.

Numerous auxin transport inhibitors (Phytotrophins) can be used including: N-(1-naphthyl)phthalamic acid "Naptalam" (NPA); 2,3,5-Triiodobenzoic acid (TIBA); 9-hydroxyfluorene-9-carboxylic acid (HFCA); Erythrosine, Eosine, Fluorescein; Semicarbazones (SCBs); and Ethanphon. Typically auxin transport inhibitors are applied at a rate of between 10 to 100% of the rate of the applied auxin derivative. In some instances rates of 200–400% of the auxin transport inhibitor relative to the applied auxin derivative is used.

Although any plant or cell can be used in the methods of the present invention, in a preferred embodiment, the plant or cell used is Brassica. A particular embodiment is Brassica which has an altered oil composition. Preferably the Brassica is one which has high oleic and low linoleic acid content such as AG019 or its relatives and derivatives.

Brassica Transformation

A novel method for obtaining transformed *Brassica napus* is also disclosed. The method is particularly useful for transformation of cultivars that have been found to be difficult to transform using previous methods. In particular the variety AG019 and progeny therefrom are preferred.

In this particular embodiment of the present invention, the subject method for obtaining transformed *Brassica napus* AG019 plants includes the steps of transformation, selection and regeneration. The method can be used to transform *Brassica napus* AG019 plants and progeny therefrom with any desired genetic material. The genetic material is inserted into a transformation vector suitable for use in Agrobacterium transformation as is known.

Transformation procedure includes co-cultivation of plant cells with a suitable strain of *Agrobacterium tumefaciens*. Strains which have been used for Brassica transformation are numerous and include, for example, strain GV3101/p MP90 (Konez & Schell, *Molecular Gen. Genet.* 204:383–396, 1986), strain LBA4404/pAL4404 (Ooms et al, *Plasmid* 7:15–29, 1992) and strain A281/pEHA105 (Hood et al., *Transgenic Res.* 2:208–218, 1983).

The Agrobacterium is used to transform Brassica cells with a selected genetic construct. The Brassica cells can be in any form, for example, cells in culture or in callus or cells in plant tissue, however, hypocotyls are preferred. The cells to be transformed are precultured. In this treatment, the cells are placed on regeneration medium for 3 days. The regeneration medium contains macro and micro nutrients, vitamins and growth regulators which induce shoot formation.

After the preculture treatment, the cells are brought into contact with a culture of the selected Agrobacterium strain. The cells are then placed onto co-cultivation media for a suitable period of time, preferably about 3 days, and preferably at a temperature of about 15° C.

After co-cultivation, the cells are transformed to callusing and recovery media for 7 days. Explants are then placed on selection medium containing macro and micro nutrients, vitamins and growth regulators which induce shoot formation. The selection medium also contains a bacteriocide, for example carbenicillin. Preferably, it also contains a selection agent. The cells are grown on the selection medium until shoots (putative transformants) develop. In the case of transformation of Brassica napus with altered oil profiles, addition of the hormone NAA to this callusing and recovery media greatly increases the formation of transgenic shoots. To enhance regeneration, any shoots which develop are transferred on a regular basis to fresh selection media. Plantlets are placed on a shoot elongation media and finally a rooting media.

The method for obtaining transformed Brassica plants described above has been found especially useful for Brassica napus AG019 varieties.

The examples set forth below are for purposes of illustration and are in no way intended to limit the scope of the invention.

EXAMPLE 1

Novel Brassica Transformation Method

The method outlined below allows convenient transformation of Brassica napus, particularly Brassica napus variety AG019 and progeny therefrom. For all steps of the AG019 Transformation Protocol the following Tissue Culture (TC) conditions are used: 22+/−1° C. under 16 hr light and 8 hr dark cycle with a light intensity of 100 microE/m2/s.

Seeds are surface sterilized for 10 s in 100% ethanol. Following the ethanol bath, the seeds are transferred to 100% Javex (5.64% w/v sodium hypochlorite)+0.1% Tween 20 (v/v) for 10 min, followed by an additional 10 min bath in 100% Javex plus 0.1% Tween 20 (v/v). The surface sterilization the seeds are then washed with approximately 800 mL of sterile water. The surface sterilized seeds are plated onto ½ strength MMOM (Murashige minimal organics medium), 1% (w/v) sucrose,0.8% (w/v) agar at pH 5.8. The surface sterilized seeds are incubated for 5–7 days under the TC conditions described above.

A single colony of Agrobacterium containing the plant transformation vector construct is transferred to AB minimal medium (Watson et al., 1975) for 48 hr at 28° C., which gives at approx. density of 6×10$^8$ cfu/mL. Hypocotyls are harvested from the germinated seeds and transferred to the Pre-Culture medium (MMOM, 3% (w/v) sucrose, 5.0 mg/L BAP, 0.7% (w/v) agar, and NAA 0.1 mg/L, pH 5.8) and incubated for 3 days under the TC conditions described above. Hypocotyl explants are then transferred from the Pre-Culture medium to the AB minimal medium containing the Agrobacterium strain of interest and incubated for at least 2 min. The hypocotyl explants are then plated back onto the pre-culture medium and incubated for 3 days under the TC conditions described above.

Following co-cultivation, the hypocotyl explants are transferred to the Callusing/Recovery medium (MMOM, 3% (w/v) sucrose, 5.0 mg/L BAP, 0.1 mg/L NAA 0.7% (w/v) agar, pH 7.5 plus 300 mg/L Timentin) and incubated under the TC conditions described above to eliminate the Agrobacterium and allow for callusing and recovery of the hypocotyl explant. It should be noted that this step includes the addition of the hormone NAA which greatly facilitates the recovery of transgenic shoots. Following Callusing/Recovery the hypocotyl explants are transferred to the Shoot Induction Medium (MMOM, 3%(w/v) sucrose, 4.5 mg/L BAP, 0.7% (w/v)agar, pH 5.8 plus 300 mg/L Timentin, 5.0 mg/L silver nitrate and a selection agent such as kanamycin if apprpriate) and incubated for approximately 4 weeks under the TC conditions described above to induce the formation of shoots. Following a 4 week incubation on the Shoot Induction medium green shoots and callus are transferred to the Shoot Elongation medium which contains MMOM, 3% (w/v) sucrose and 0.7% (w/v) agar plus 300 mg/L Timentin, plus a selection agent at pH 5.8. The green shoots and callus are incubated for an additional 4 weeks using the TC conditions as described above. Green shoots are transferred from the Shoot Elongation medium to the Rooting medium (MMOM, 3% (w/v) sucrose and 0.7% (w/v) agar; 0.1 mg/L NAA, or IBA; pH 7.5) and incubated for an additional 4 weeks or until roots have developed for transfer to soil. Following root formation the plantlets are transferred to soil and grown under greenhouse conditions.

EXAMPLE 2

Construction of a Novel Plant Transformation Vector Comprising a Conditionally Lethal Gene (Oncogene 2)

Novel plant transformation vectors comprising the oncogene 2 from Agrobacterium as a conditionally lethal gene were constructed, as described in this Example and Examples 3 to 7. These vectors allow plants transformed with them to be selectively removed from a population of untransformed plants. Such features as conferred by these vectors are not found in vectors routinely employed for producing transgenic Brassica plants.

The vector is prepared by first isolating the conditionally lethal oncogene 2 from Agrobacterium tumifaciens strain A248 by PCR and introducing restriction sires at the 5' and 3' end of the gene. A DNA coding sequence, along with the native promoter and terminator sequence from the plasmid pTiA6 was obtained from Genbank (Accession No. X00409).

Total DNA was extracted from Agrobacterium tumefaciens strain A248. A 2.3 Kb PCR product extending from a Hind III site near the 5' end of Oncogene 1 (IAA-M), through the full length bidirectional promoter, through the coding region of oncogene 2 (IAA-H), ending with its terminator, was amplified from Ti plasmid pTiA6. The primers used, pr8349 and pr7495, were designed using the published sequence of oncogene2. (GenBank accession no. X00409). To facilitate cloning the product, 5' extensions on the primers introduced three restriction sites, XbaI, Pst I and Kpn I, to the 5' end and a BamHI site to the 3' end of the resulting PCR product.

```
                              KpnI
                 XbaI    PstI
pr8349 5'-AAAATCTAGACTGCAGGTACCGCACTCGGTGGAGATTTG3'

BamHI
pr7495 5'-AAAAGGATCCCACAGCGTGTGCCTAAATAGGATTGCT-3'
```

Total DNA from Agrobacterium strain A248 is used in a PCR reaction containing 0.1 ug of template DNA, 5 units (1 uL) of TaqPlus DNA Polymerase from Stratagene (San Diego, Calif.), 10 ul of Extend Taq Buffer (Stratagene), 0.5

U (0.2 ul) of Pfu DNA polymerase (Stratagene), 8 ul of 2.5 mM dNTPs, 5 uM primers (2.5 ul of each) and 21.2 ul of water. The reaction is initiated at 94° C. for 2 minutes, then 35 cycles of: 94° C. for 30 seconds, 55° C. for 30 seconds, 72° C. for 2 minutes. Following these cycles, the reaction is held at 72° C. for 7 minutes and the DNA is isolated.

A 1.8 Kb product is obtained which was verified by restriction analysis to correspond to authentic oncogene 2.

The PCR product was digested with XbaI and Bam HI and ligated into the corresponding sites of plasmid pHS723 (Hirji, R., Hammerlindl, J. K., Woytowich, A. E., Khachatourian, G. G., Datla, R. S. S., Keller, W. A., Selveraj, G. (1996) Plasmid pHS723 and its derivatives: plant transformation vectors that enable efficient selection and progeny analysis. Fourth Canadian Plant Tissue Culture and Genetic Engineering Conference, Saskatoon, Saskatchewan, Canada) to give pJH121. The resulting vector was transferred to Agrobacterium strain GV3101::pMP90 and used in co-cultivation experiments to produce transformed plants expressing Oncogene 2. The vector also confers kanamycin resistance and GUS activity for screening of transgenics. The derivation of pJH121 is illustrated in FIG. 1.

EXAMPLE 3

Construction of Plant Transformation Vector pJH122

Figure 2:
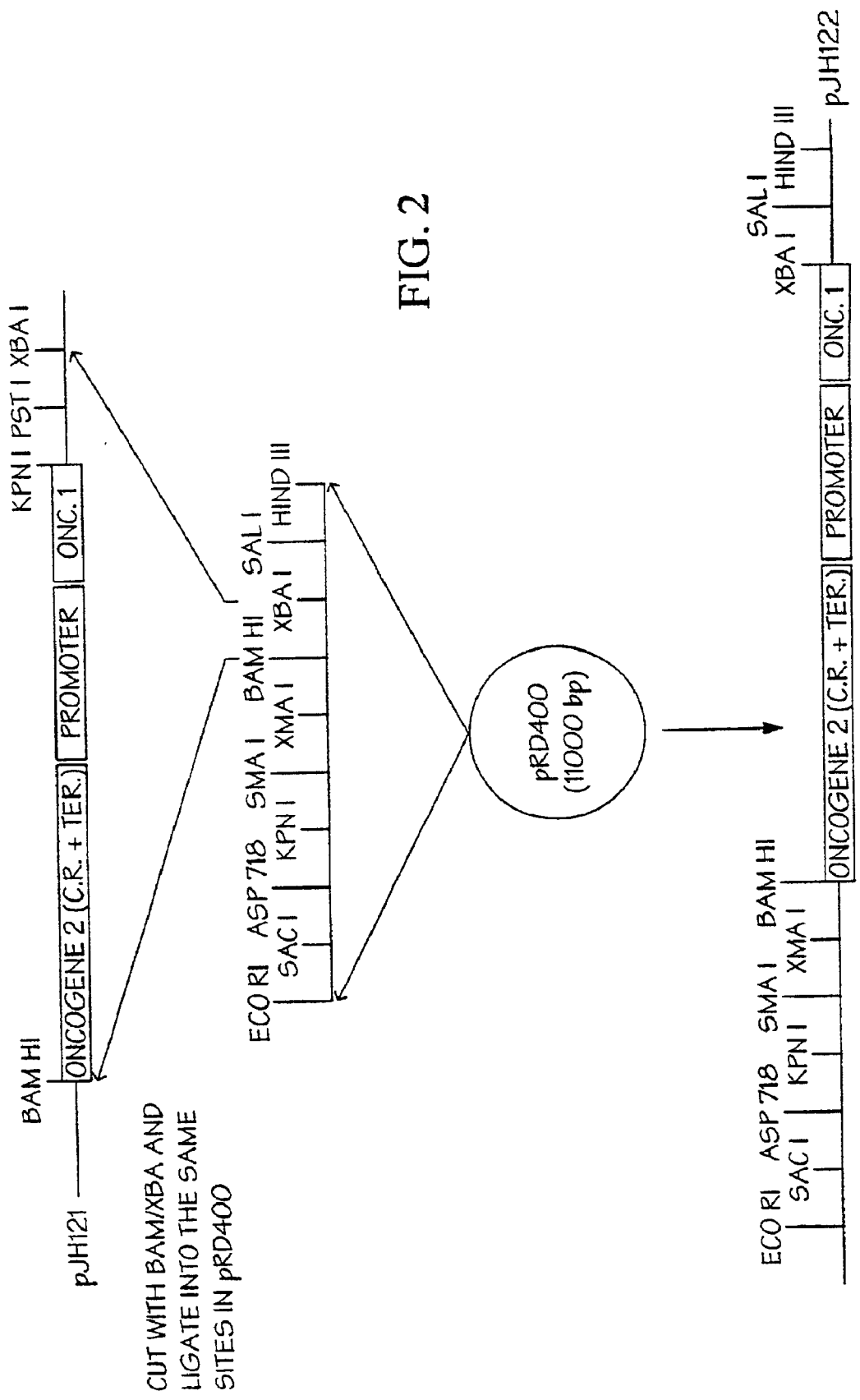
FIG. 2 illustrates the construction of the plant transformation vector pJH122 comprising the conditionally lethal Agrobacterium oncogene 2 in the vector pRD400. In addition to the oncogene, the vector contains the kanamycin resistance gene for the selection of plant cells.

A plant transformation vector comprising oncogene 2 and a kanamycin resistance marker was constructed as follows. Plasmid pJH121 was digested sequentially first with Xba I, then BamHI to excise the 2.3 Kb oncogene 2 coding region and terminator driven by its native, full length promoter. The fragment was gel purified and electroeluted The binary plant transformation vector pRD400 was similarly digested with Xba I and Bam HI. pRD400 is a plasmid identical to pBIN 19 except a single base pair has been changed in the neomycin phosphotransferase gene to enhance expression of the selectable marker (Datla et al, *Gene* 122: 383–384, 1992). The electroeluted oncogene cassette was ligated into the corresponding sites of the vector. The resulting plasmid, pJH122, was transferred by triparental mating into Agrobacterium strain GV3101::pMP90 for transformation to plants. Derivation of pJH122 is illustrated in FIG. 2.

EXAMPLE 4

Construction of Plant Transformation Vector pJH123

A plant transformation vector comprising a conditionally lethal gene and a gene encoding a heterologous protein capable of expression in plant cells was constructed. In this example the conditionally lethal oncogene 2 was joined to a heterologous gene encoding a fusion protein. The fusion in this case is between the oleosin gene and the beta glucuronidase gene, under the control of the oleosin promoter in the plasmid SBS 2002. Plasmid SBS 2002 is a plant transformation vector which contains a 3.8 kb cassette consisting of an Arabidopsis oleosin promoter and coding region which is translationally fused to the beta glucuronidase coding region and ends in the nopaline synthase terminator. The cassette is essentially as it appears in pCGYOBPGUSA, described in van Rooijen and Moloney (Structural requirements of oleosin domains for subcellular targeting to the oil body. Plant Physiology 109 (1995): 1353–1361). The plasmid SBS2002 was digested with Pst I and the fragments separated on agarose gel. The 3.8 kb Oleosin-GUS-NOS ter. cassette was electroeluted and ligated to Pst I—Bgl II adapters. The adapters were phosphorylated on the Pst I end but not on the Bgl II end. The resulting product was then phosphorylated at the Bgl II sites by a kinase reaction. Plant transformation vector pJH122 as described in example 3 was digested with Bam HI and dephosphorylated. The kinased Oleosin-GUS fragment was then ligated into the Bam HI sites of the vector in the presence of Bam HI enzyme. Only the Bam/Bgl ligations will survive when transformed into *E. coli*.

Figure 3:
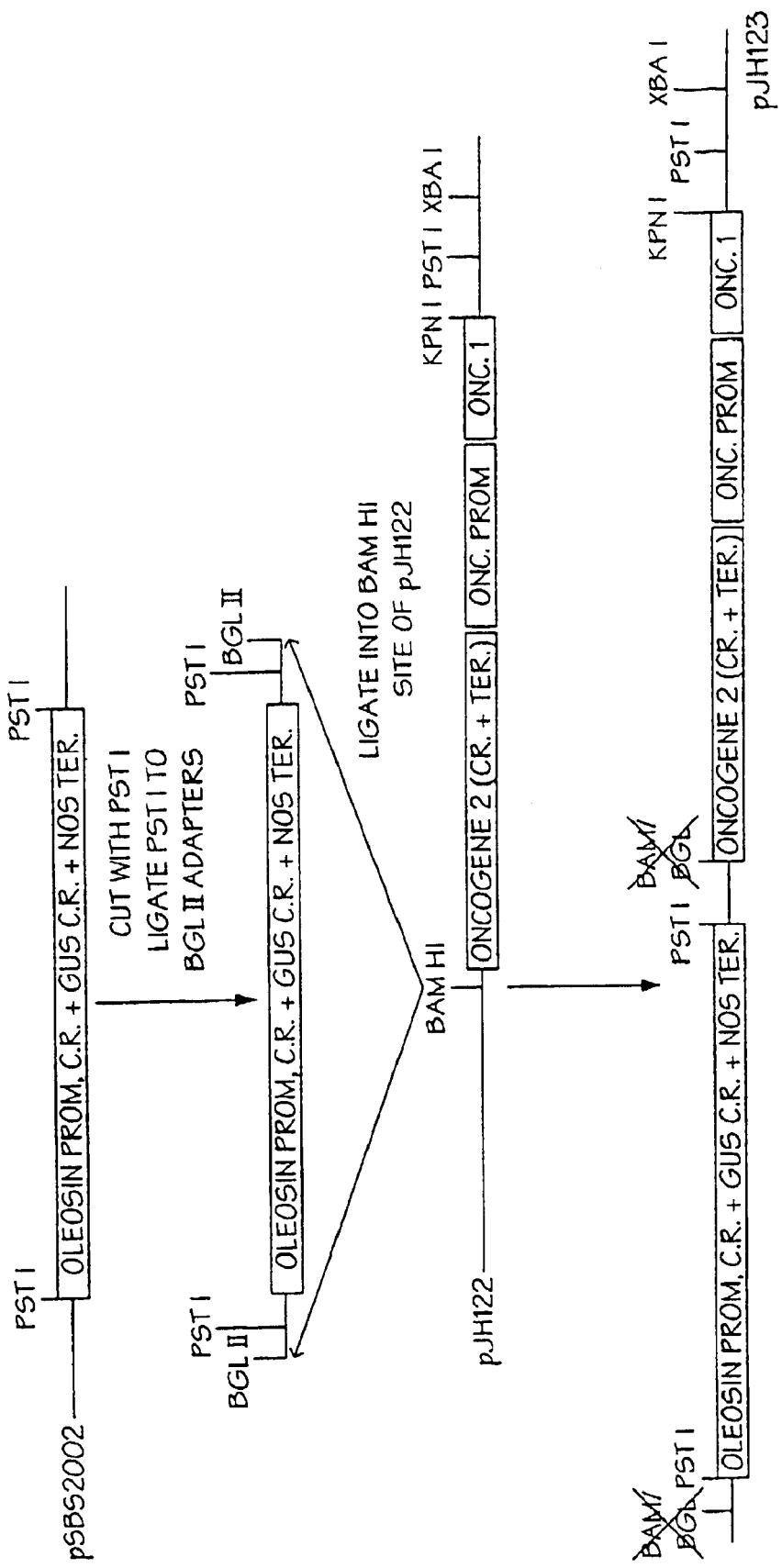
FIG. 3 illustrates the derivation of the plant transformation vector pJH123 comprising the conditionally lethal Agrobacterium oncogene 2 linked to a heterologous gene which is an Arabidopsis seed oleosin coding region fused in-frame to the GUS coding sequence. The seed oleosin coding region provides specific localization of the fusion protein to seed oil bodies. The heterologous gene is under control of the seed oleosin promoter.

The finished vector, pJH123, was transferred by triparental mating to Agrobacterium strain GV3101:pMP90 for plant transformations. The vector confers on transformed tissue and plants, kanamycin resistance for selection as well as expression of Oncogene 2. In addition, the oleosin-GUS cassette provides for expression of glucuronidase activity targeted to the oil bodies of seeds (van Rooijen and Moloney, 1995). The derivation of pJH123 is illustrated in FIG. 3.

EXAMPLE 5

Construction of Plant Transformation Vector PJH125

The region extending from the translational start codon of the coding region of oncogene 2 and ending with its terminator was amplified by PCR from Ti plasmid pTiA6 which was extracted from the total DNA of *Agrobacterium tumefaciens* strain A248. The primers used, pr10109 and pr7495, were designed using the published sequence of oncogene2. (GenBank accession no. X00409). To facilitate cloning the product, 5' extensions on the primers introduced two restriction sites, XbaI and NcoI, to the 5' end and a BamHI site to the 3' end of the resulting PCR product.

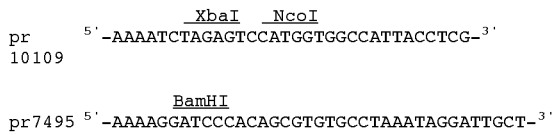

Figure 4:
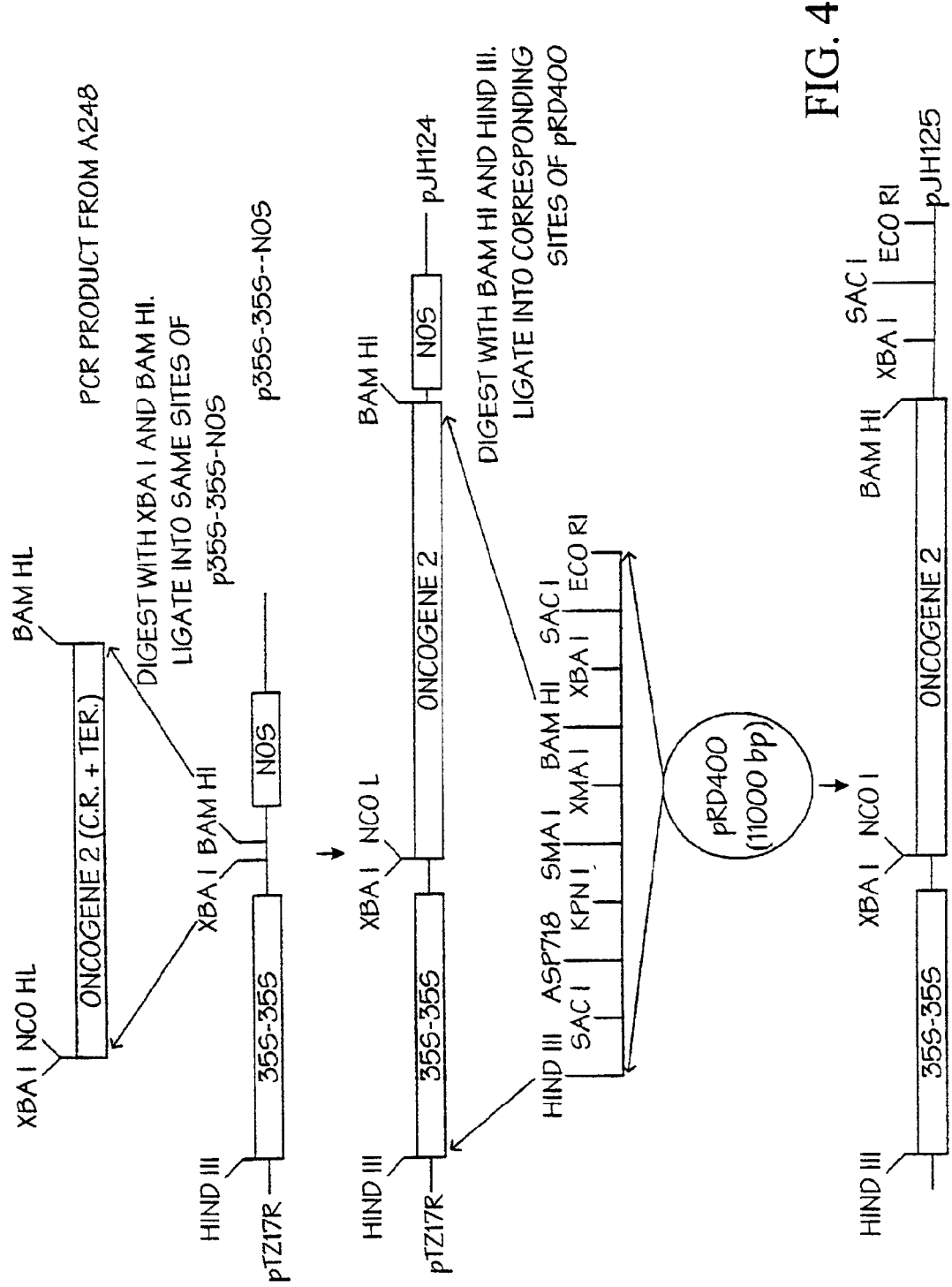
FIG. 4 illustrates construction of the plant transformation vector pJH125, comprising the conditionally lethal Agrobacterium oncogene 2 under the control of the 35S promoter, in the vector pRD400. In addition to the oncogene, the vector contains the kanamycin resistance gene for selection of plant cells.

The PCR product was digested with XbaI and Bam HI and ligated into the corresponding sites of plasmid p35S-35S-NOS. The plasmid p35S-35s-NOS comprises a 600 bp fragment consisting of the 35S cauliflower mosaic promoter with duplicated enhancer sequence (Kay, R., Chan, A., Daly, M., and McPherson, J., Duplication of CaMV 35S Promoter sequences creates a strong enhancer for plant genes. Science, 236 (1987) 1299–1302) and the NOS terminator. The promoter-terminator fragment is contained within the common cloning vector pTZ17R and was obtained from Dr. Raju Datla (Plant Biotechnology Institute, National Research Council of Canada, 110 Gymnasium Road, Saskatoon, Saskatchewan, S7N 0W9) to give pJH124. The 2300 bp promoter-oncogene cassette was isolated from pJH124 as a HindIII to BamHI fragment and ligated into the corresponding sites of the multiple cloning site of binary plant transformation vector pRD400 to derive plant transformation vector pJH125. The vector was transferred to Agrobacterium strain GV3101:pMP90 and used in co-cultivation with explants to produce transformed plants expressing oncogene 2. The derivation of pJH125 is illustrated in FIG. 4.

EXAMPLE 6

Construction of Plant Transformation Vector pJH126

The Oleosin-GUS cassette from pSBS 2002 was isolated, Tinkered and kinased as described for the construction of pJH123. Plant transformation vector pJH126 (consisting of pRD400 containing the oncogene 2 coding region and terminator driven by the 35S—35S promoter) was digested with BamHI and dephosphorylated. The kinased Oleosin-GUS fragment was then ligated into the dephosphorylated BamHI sites of the vector in the presence of Ba HI enzyme as described for pJH123.

Figure 5:
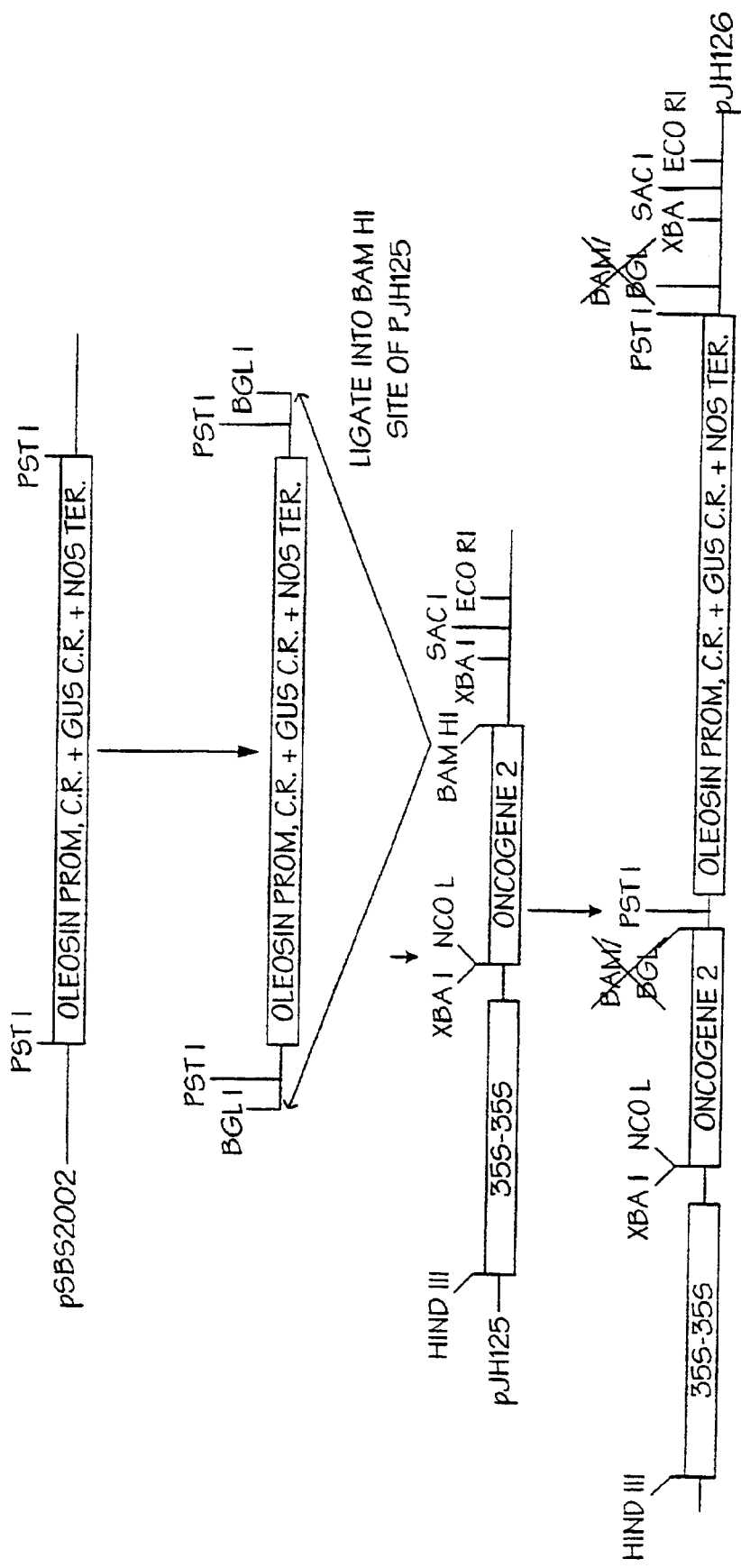
FIG. 5 illustrates the derivation of the plant transformation vector pJH126 comprising the conditionally lethal Agrobacterium oncogene 2, under the control of the 35S promoter, linked to a heterologous gene which is an Arabidopsis seed oleosin coding region fused in-frame to the GUS coding sequence. The seed oleosin coding region provides specific localization of the fusion protein to seed oil bodies. The heterologous gene is under control of the seed oleosin promoter.

The finished vector, pJH126, was transferred by triparental mating to Agrobacterium strain GV3101::pMP90 for plant transformations. The vector confers on transformed tissue and plants kanamycin resistance for selection as well as expression of oncogene 2. In addition, the Oleosin-GUS cassette provides expression of glucuronidase activity targeted to the oil bodies of seeds. The derivation of pJH126 is illustrated in FIG. 5.

EXAMPLE 7

Construction of Plant Transformation Vector pJH130

Figure 6:
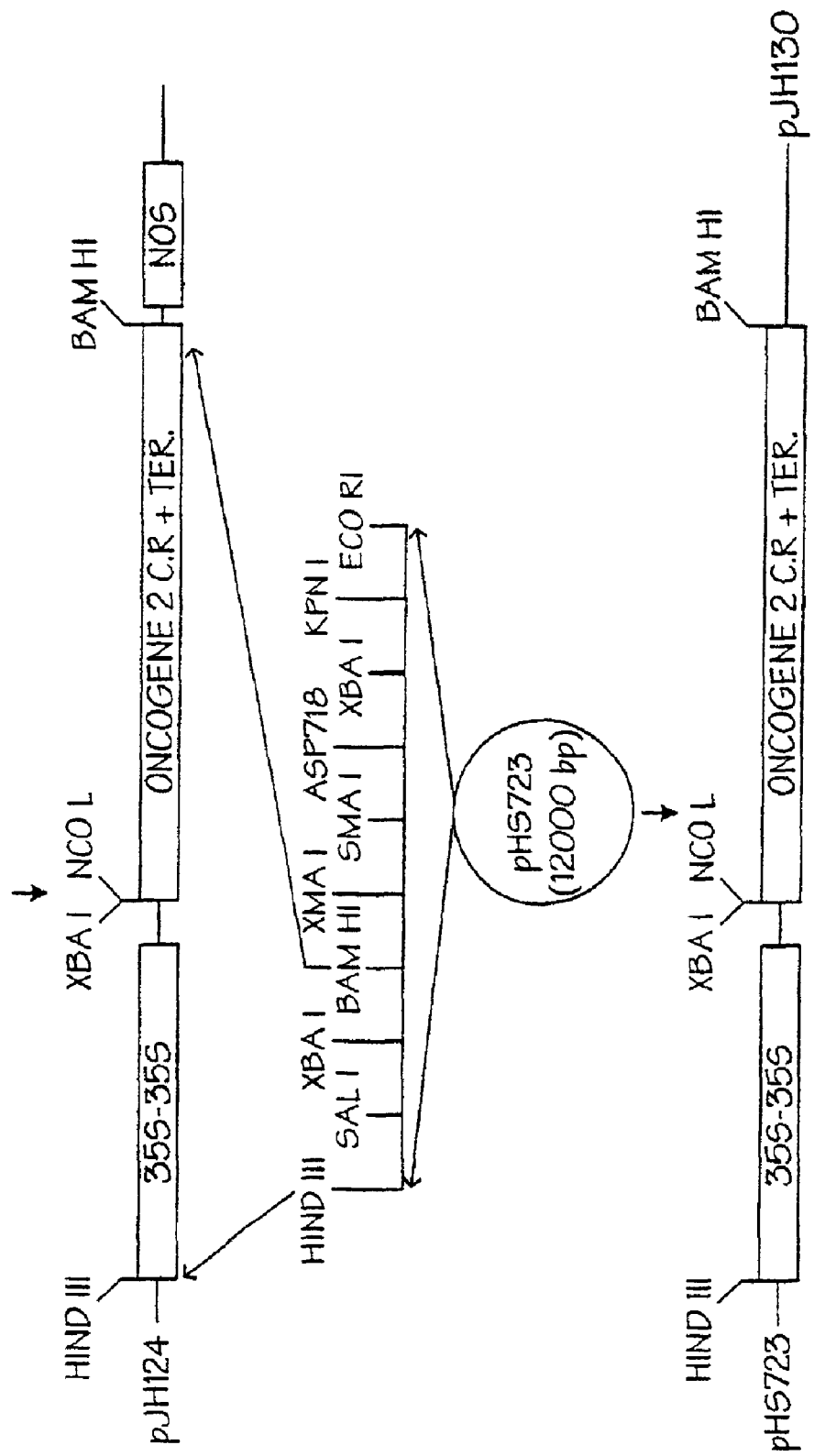
FIG. 6 illustrates construction of the plant transformation vector pJH130 comprising the conditionally lethal Agrobacterium oncogene 2, under the control of the 35S promoter, in the vector pHS723. In addition to the oncogene, the vector contains a gene encoding the beta glucuronidase—kanamycin resistance fusion protein for the selection of plant cells.

The 2300 bp 35S—35S promoter-oncogene cassette was isolated as a HindIII to BamHI fragment from pJH124 and cloned into the corresponding sites of plant transformation vector pHS723 to produce plasmid pJH130. The backbone vector, pHS723, expresses a GUS/NPT fusion protein which allows the selection of transformed cells, plants and their progeny based on kanamycin resistance and the facile screening of transformed tissue based on expression of glucuronidase activity. With the introduced oncogene cassette, the cells, plants and their progeny also express additionally the oncogene 2 gene product. The derivation of pJH130 is illustrated in FIG. 6.

EXAMPLE 8

Analysis of Transformed Tobacco Plants Containing the Vector pJH121

Transformed tobacco plants containing the pJH 121 construct described above are recovered and tested using standard analysis to determine the presence of the inserted vector. Confirmed transformants are selected and a representative number of plants are treated with NAM to demonstrate the conditionally lethal phenotype as follows. A solution containing 200 ug/mL of NAM with 0.1% Tween 20 is prepared. Plants were sprayed to runoff using a pressurized sprayer. In plants expressing the conditionally lethal phenotype, 2 days after spraying the leaves are drooping and the leaf margins curling. Within 5 days the leaves are twisted and the plant shows typical auxin toxicity. Non-transformed plants are unaffected by the treatment.

Seed is collected from transformed plants and germinated in the presence of NAM to confirm seed expression of the conditionally lethal phenotype.

EXAMPLE 9

Analysis of Transformed *Brassica napus* Plants Containing the Vector pJH121

Transformed *Brassica napus* plants containing the construct pJH 121 described above are recovered and tested using standard analysis to determine the presence of the inserted vector. Confirmed transformants are selected and a representative number of plants at the three-four leaf stage of growth are treated with NAM to demonstrate the conditionally lethal phenotype as follows. A solution containing 200 ug/mL of NAM with 0.1% Tween 20 is prepared. Plants were sprayed to runoff using a pressurized sprayer. In plants expressing the conditionally lethal phenotype, the transgenic plants remained stunted in growth 25 days after spraying while the non-transgenic varieties grew normally and flowered.

Seed is collected from transformed plants and germinated in the presence of NAM to confirm seed expression of the conditionally lethal phenotype.

EXAMPLE 10

Analysis of Transformed *Brassica napus* Containing the Vector pJH125

Transformed *Brassica napus* plants containing the construct pJH 125 (35S oncogene 2) described above are recovered and tested using standard analysis to determine the presence of the inserted vector. Confirmed transformants are selected and a representative number of plants are treated with NAM to demonstrate the conditionally lethal phenotype as follows. A solution containing 200 ug/mL of NAM with 0.1% Tween 20 is prepared. Plants were sprayed to runoff using a pressurized sprayer. In plants expressing the conditionally lethal phenotype, 2 days after spraying the leaves are drooping and the leaf margins curling. Within 5 days the leaves are twisted and the plant shows typical auxin toxicity. Non-transformed plants are unaffected by the treatment.

EXAMPLE 11

Demonstration of Oncogene 2 as a Positive Selectable/Scorable Marker in Breeding Programs Oncogene 2, when linked to the trait transgene of interest, can be used as a positive selectable and scorable marker in transformation, event conversion, and conventional breeding strategies as a simple visual marker for tracking the trait gene of interest. The ability to visually select plants in an event conversion (backcross, introgression) and conventional breeding programs reduces the time and analytical support (ELISA; PCR; Southern Blot Analysis, etc.) required to identify the progeny that contain the transgene of interest from crosses between the transgenic event and agronomically elite germplasm. Furthermore, the rapid visual selection in a breeding program reduces tissue sample handling and maintenance of non-transgenic plants in a segregating population that are not of interest in the breeding program until the results of the analytical analysis are available from the laboratory.

In this example, 20 plants from JH 2984 and JH 2973 transformation events were planted. These transgenic varieties were segregating 3:1 for the inserted plant transformation vector pJH 125. NAM was applied at a rate of 1 mg/mL at the 2–3 leaf stage. 24 hours after application of NAM, plants were scored for a visual phenotype. From the visual appearance of twisted leaves, a random sampling of 8 plants were chosen as being putative transgenics, 4 chosen as being non-transgenic. These plants were subjected to PCR analysis for the presence of the transformation vector. All 8 putative transgenic plants were confirmed to carry the transformation vector by PCR, whereas all four of the putative nulls, or non-transgenic plants were shown to be non-transgenic by PCR analysis. Thus the rapid and reliable use of oncogene 2 as a scorable marker to identify transgenic varieties within segregating populations (e.g. such as breeding programs or during introgression) is demonstrated.

EXAMPLE 12

Use of the Conditionally Lethal Oncogene 2 as a Scorable Marker in Embryo and Seed Germination Oncogene 2 can be used as a selectable marker in seed germination and embryo rescue in vitro assays, allowing for an even earlier determination of the presence of the transformation vector in segregating populations. Seeds or embryos of transgenic plants containing pJH 125, when cultured on a medium containing NAM and an auxin transport inhibitor can be visually selected on basis of phenotype when compared to non-transformed seedlings. The in vitro assay reduces the time and physical space (e.g. number of plants in growth chambers or under cultivation) required to identify homozygous transgenic lines, and the embryo rescue method allows selection and recovery of transformed seedlings which reduces generation to generation cycle time a breeding program.

In this example, seeds from JH2973 and JH2984, representing a segregating population for the transformation vector pJH 125 were germinated in vitro in the presence of NAM and the auxin transport inhibitor naphthylphthalamic acid (NPA). Transgenic seedlings are selected on the basis of phenotype that includes stunted seedlings, small cotyledons, stunted and swollen roots and callus at the root/shoot junction. Non-transformed segregants grew normally. When the putative transgenic seedlings were transferred to non-selective media, plants recovered and grew normally. The presence of the transformation vector in these plants was confirmed as above.

It is obvious that for *Brassica napus,* the use of microspore culture to produce microspore derived embryos in combination with the use of oncogene 2 as a scorable marker provides a convenient means to derive homozygous transgenic lines.

EXAMPLE 13

Use of Oncogene 2 as a Selectable Marker During the Transformation of *Brassica napus*

The transformation protocol detailed in example 1 can be modified to allow the use of oncogene 2 within the procedure. In particular, the transformation protocol described in example 1 requires treatment with NAA at the pre-culture, co-cultivation, callusing/recovery, and root induction phases for the successful recovery of transgenic varieties of AG019 and progeny therefrom. Replacement of NAA with NAM, in the callusing and recovery 7 day period of incubation in those instances where the oncogene 2 is included in the transformation vector provides a convenient means of promoting the growth of the transgenic plant cells and provides a positive selection method for the recovery of transgenic Brassica. The media is made up with NAM in place of NAA and typically includes an auxin transport inhibitor at a ratio of 1:2 to 2:1 (NAM:Auxin Transport Inhibitor).

Each patent, patent application and publication mentioned hereinbefore is herein individually incorporated by reference.

Modifications to the foregoing specific embodiments will be evident to persons skilled in the art, while carrying out the teachings of the invention. It is intended that all such modifications be covered by the claims appended hereto.

What is claimed is:

1. A genetic construct, comprising:
   a conditionally lethal first gene expressible in a plant cell of a plant, said conditionally lethal first gene being a gene encoding indoleacetamide hydrolase (IAMH); and
   a second gene expressible in said plant cell, said second gene, when expressed in said plant cell, conferring a non-naturally occurring trait of interest on said plant cell, said second gene being selected from the group consisting of:
   (a) a gene which, when expressed in said plant cell, confers insect resistance on said plant cell;
   (b) a gene which, when expressed in said plant cell, confers an output trait on said plant cell;
   (c) a gene encoding an industrially useful enzyme;
   (d) a gene encoding a pharmaceutically active compound;
   (e) a gene encoding rennin or hirudin; and
   (f) a gene encoding an antisense RNA.

2. The genetic construct of claim 1, wherein the second gene is a gene which, when expressed in said plant cell, confers insect resistance on said plant cell.

3. The genetic construct of claim 1, wherein the second gene codes for a pharmaceutically active compound.

4. The genetic construct of claim 1, wherein the second gene codes for an industrially useful enzyme.

5. The genetic construct of claim 1, wherein the second gene codes for rennin or hirudin.

6. The genetic construct of claim 1, wherein the second gene is a gene which, when expressed in said plant cell, confers an output trait on said plant cell.

7. The genetic construct of claim 1, wherein the second gene codes for an anti-sense RNA.

8. The genetic construct of claim 6, wherein said output trait is selected from the group consisting of altered oil or meal composition, reduced antinutritional content, and altered processing characteristics.

9. The genetic construct of claim 1, wherein the gene encoding IAMH is oncogene 2 from *Agrobacterium tumefaciens*.

10. The genetic construct of claim 1, wherein the conditionally lethal gene is adapted to be expressed in said plant in response to a chemical or physiological stress applied to said plant cell.

11. The genetic construct of claim 1, wherein the conditionally lethal gene is configured to express a gene product lethal to said plant upon application of an exogenous substance to said plant cell.

12. The genetic construct of claim 1, further comprising an inducible promoter in operable association with said conditionally lethal first gene.

13. The genetic construct of claim 1, further comprising a tissue-specific promoter in operable association with said conditionally lethal first gene.

14. A plant transformation vector comprising the genetic construct of claim 1.

15. A transgenic plant, comprising:
   a conditionally lethal first gene expressible in a plant cell of said transgenic plant, said conditionally lethal first gene being a gene encoding indoleacetamide hydrolase (IAMH); and
   a second gene expressible in said plant cell of said transgenic plant, said second gene, when expressed in said plant cell, conferring a non-naturally occurring trait of interest on said plant cell, said second gene being selected from the group consisting of:
   (a) a gene which, when expressed in said plant cell, confers insect resistance on said plant cell;
   (b) a gene which, when expressed in said plant cell, confers an output trait on said plant cell;
   (c) a gene encoding an industrially useful enzyme;
   (d) a gene encoding a pharmaceutically active compound;
   (e) a gene encoding rennin or hirudin; and
   (f) a gene encoding an antisense RNA.

16. A method for selectively removing at least one plant from a growing environment, comprising:
   transforming at least one plant cell with a genetic construct including:
      a conditionally lethal first gene expressible in said at least one plant cell, said conditionally lethal first gene being a gene encoding indoleacetamide hydrolase (IAMH); and
      a second gene expressible in said at least one plant cell, said second gene, when expressed in said at least one plant cell, conferring a non-naturally occurring trait of interest on said at least one plant cell, said second gene being selected from the group consisting of:
      (a) a gene which, when expressed in said plant cell, confers insect resistance on said plant cell;
      (b) a gene which, when expressed in said plant cell, confers an output trait on said plant cell;
      (c) a gene encoding an industrially useful enzyme;
      (d) a gene encoding a pharmaceutically active compound;
      (e) a gene encoding rennin or hirudin; and
      (f) a gene encoding an antisense RNA.;
   regenerating the at least one plant cell to at least one whole plant; and
   applying a chemical agent to said at least one whole plant, said chemical agent being configured to be converted into a phytotoxic agent of said at least one whole plant by one or more gene products of said conditionally lethal gene, wherein said chemical agent comprises an indoleamide or a related auxin derivative that is a substrate for IAMH.

17. The method of claim 16, wherein said applying said chemical agent comprises applying said chemical agent in an amount selected to effect a sub-lethal level of said phytotoxic agent in said at least one whole plant upon said conversion by said one or more gene products of said conditionally lethal gene.

18. The method of claim 17, further comprising visually identifying a sub-lethal phenotype of said at least one whole plant.

19. The method of claim 16, wherein the chemical agent is naphthalene acetamide.

20. A method for selecting a germinating seed or plant embryo comprising a transgene, comprising:
   providing at least one tranagenic plant cell of a plant seed or plant embryo, said at least one transgenic plant cell including a transgene encoding indoleacetamide hydrolase (IAMH);
   culturing the at least one transgenic plant cell on a medium comprising an auxin transport inhibitor and an indoleamide or a related auxin derivative that is a substrate for IAMH; and
   visually identifying the at least one transgenic plant cell by its expression of a sub-lethal auxin-overproduction phenotype.

21. The method of claim 20, wherein the auxin transport inhibitor is selected from the group consisting of N-(1- naphthyl)phthalamic acid, 2,3,5-triiodobenzoic acid, 9-hydroxyfluorene-9-carboxylic acid, erythrosine, eosine, fluorescein, semicarbazone, and ethanphon.

22. The method of claim 20, wherein said indoleamide or related auxin derivative that is a substrate for IAMH is naphthalene acetamide and the auxin transport inhibitor is naphthylphthalamic acid.

23. The method of claim 20, wherein the at least one plant cell comprises a seed or a plant embryo.

24. The method of claim 20, further comprising transferring the at least one transgenic plant cell to a second medium free from indoleamide and recovering the at least one transgenic plant cell.

25. The method of claim 24, wherein the second medium comprises naphthalene acetic acid.

26. The method of claim 20, further comprising transforming at least one plant cell with oncogene 2 of *Agrobacterium tumefaciens* to obtain said at least one transgenic plant cell.

27. A method for producing a transgenic plant comprising a transgene encoding indoleacetamide hydrolase (IAMH), comprising:
 providing at least one transgenic plant cell of a plant seed or plant embryo, said at least one transgemc plant cell including a transgene encoding IAMH;
 culturing the at least one transgenic plant cell on a medium comprising naphthalene acetamide and an auxin transport inhibitor;
 visually identifying the at least one transgenic plant cell by its expression of a sub-lethal auxin-overproduction phenotype; and
 transferring the at least one transgenic plant cell to a second medium comprising naphthalene acetic acid to recover the at least one transgenic plant cell.

28. The transgenic plant of claim 15, wherein the second gene is a gene which, when expressed in said plant cell, confers insect resistance on said plant cell.

29. The transgenic plant of claim 15, wherein the second gene codes for a pharmaceutically active compound.

30. The transgenic plant of claim 15, wherein the second gene codes for an industrially useful enzyme.

31. The transgenic plant of claim 15, wherein the second gene codes for rennin or hirudin.

32. The transgenlc plant of claim 15, wherein the second gene is a gene which, when expressed in said plant cell, confers an output trait on said plant cell.

33. The transgenic plant of claim 15, wherein the second gene codes anti-sense RNA.

34. The transgenic plant of claim 15, wherein said output trait is selected from the group consisting of altered oil or meal composition, reduced antinutritional content, and altered processing characteristics.

35. The transgenic plant of claim 15, wherein the gene encoding IAMH is oncogene 2 from *Agrobacterium tumefaciens*.

36. The transgenic plant of claim 15, wherein the conditionally lethal gene is adapted to be expressed in said plant in response to a chemical or physiological stress applied to said plant.

37. The transgenic plant of claim 15, wherein the conditionally lethal gene is configured to express a gene product lethal to said plant upon application of an exogenous substance to said plant cell.

* * * * *

UNITED STATES PATENT AND TRADEMARK OFFICE
CERTIFICATE OF CORRECTION

PATENT NO.     : 6,753,459 B2
DATED          : June 22, 2004
INVENTOR(S)    : Wilfred A. Keller et al.

It is certified that error appears in the above-identified patent and that said Letters Patent is hereby corrected as shown below:

<u>Column 28,</u>
Line 14, after "...the second gene codes..." insert -- ...for an... --.

Signed and Sealed this

Tenth Day of January, 2006

JON W. DUDAS
*Director of the United States Patent and Trademark Office*